US011523856B2

United States Patent
Dai et al.

(10) Patent No.: US 11,523,856 B2
(45) Date of Patent: Dec. 13, 2022

(54) PLASMA GUN FOR TREATING TUMORS IN VIVO AND USE METHOD THEREOF

(71) Applicant: Wuxi Daixifen Biotechnology Co., Ltd, Jiangsu (CN)

(72) Inventors: Xiaofeng Dai, Jiangsu (CN); Shaoqing Xiao, Jiangsu (CN)

(73) Assignee: JIANGSU CAPTAIN BIOTECHNOLOGY CO., LTD., Nanjing (CN)

( * ) Notice: Subject to any disclaimer, the term of this patent is extended or adjusted under 35 U.S.C. 154(b) by 852 days.

(21) Appl. No.: 16/367,484

(22) Filed: Mar. 28, 2019

(65) Prior Publication Data

US 2019/0298431 A1 Oct. 3, 2019

(30) Foreign Application Priority Data

Mar. 29, 2018 (CN) .......................... 201810274260.6

(51) Int. Cl.
*H01J 37/32* (2006.01)
*A61B 18/04* (2006.01)

(52) U.S. Cl.
CPC ........ *A61B 18/042* (2013.01); *H01J 37/3244* (2013.01); *H01J 37/32082* (2013.01); *H01J 37/32541* (2013.01); *H01J 2237/026* (2013.01)

(58) Field of Classification Search
CPC ............. H01J 37/3244; H01J 37/32541; H01J 37/32082; H01J 37/32623; H01J 37/32532; H01J 37/32889; A61B 18/042
See application file for complete search history.

(56) References Cited

U.S. PATENT DOCUMENTS

| 10,730,239 B1* | 8/2020 | Glukhoy | B22F 10/10 |
| 2010/0100091 A1* | 4/2010 | Truckai | A61B 18/042 606/33 |
| 2010/0125267 A1* | 5/2010 | Lee | A61B 18/14 315/111.21 |
| 2012/0187841 A1* | 7/2012 | Kindel | A61B 18/042 315/111.21 |
| 2013/0261536 A1* | 10/2013 | Sartor | A61B 18/042 604/23 |

(Continued)

FOREIGN PATENT DOCUMENTS

| CN | 203001102 U | 6/2013 |
| CN | 103189008 A | 7/2013 |
| CN | 107106225 A | 8/2017 |

Primary Examiner — Tung X Le

(57) ABSTRACT

A plasma gun for treating a tumor in vivo and a use method thereof. The plasma gun includes a generator component including an ionization device and a shield element, and a discharge component. The ionization device is provided at the shield element, and the discharge component is connected to an end of the shield element. The present invention overcomes the problem that a low-temperature plasma jet cannot contact a tumor in vivo. The plasma gun reaches the interior of the tumor, promoting the treatment of the plasma to the tumors. It is suitable for the application in clinical treatment. As compared with the conventional radiotherapy, chemotherapy and surgery, the present invention has the advantages of selectivity on cancer cells and little side effects. The plasma directly reaches the tumor lesion, which has good therapeutic effect and avoids the impact on normal tissues.

7 Claims, 13 Drawing Sheets

(56) References Cited

U.S. PATENT DOCUMENTS

| | | |
|---|---|---|
| 2014/0378892 A1 | 12/2014 | Keidar et al. |
| 2015/0238248 A1* | 8/2015 | Thompson ........... A61B 18/042 606/50 |
| 2017/0354453 A1* | 12/2017 | Krasik ................. A61B 18/042 |
| 2018/0035893 A1* | 2/2018 | Donner ................ A61B 5/4571 |
| 2019/0262058 A1* | 8/2019 | Cheng ............... H01J 37/32623 |

* cited by examiner

PLASMA GUN FOR TREATING TUMORS IN VIVO AND USE METHOD THEREOF

CROSS-REFERENCE TO RELATED APPLICATIONS

This application claims the benefit of priority from Chinese Patent Application No. CN201810274260.6, filed on Mar. 29, 2018. The content of the aforementioned application, including any intervening amendments thereto, is incorporated herein by reference in its entirety.

TECHNICAL FIELD

The present invention relates to medical devices, and in particular to a plasma gun for treating tumors in vivo and a use method thereof.

BACKGROUND OF THE INVENTION

Plasma is a fully ionized or partially ionized matter including positive ions and negative ions, free electrons, free radicals, ozone, ultraviolet radiation, etc. Plasma is called the fourth state of matter after the states of solid, liquids and gases. At present, the technology under research has enabled plasma to form at atmospheric pressure, especially form a low temperature atmospheric plasma, which makes its application in biology possible. The low-temperature atmospheric plasma can produce an effective amount of moderate active substances to act on cancer cells, promoting apoptosis of cancer cells through oxidative stress and inhibiting the cancer cell growth and metastasis with little damage to normal cells. Conventional chemoradiotherapy kills fast-growing cells, but it is not very specific to cancer cells and causes great pain to patients during treatment. The low-temperature atmospheric plasma is quite moderate, making it a potential cancer physiotherapy to be developed. In recent years, plasma medicine has developed into a subject, and papers on low-temperature plasma in the medical field have been published increasingly. The low-temperature plasma shows some effect in clinical cancer treatment, and is expected to be an alternative effective physical means for treating cancers. Currently, the treatment using low-temperature atmospheric plasma has significant anticancer activities to about 20 kinds of cancer cells in which brain cancer, skin cancer, breast cancer, colorectal cancer, lung cancer, cervical cancer, leukemia, liver cancer, and head and neck cancer have been intensively studied. Although the low-temperature plasma has been proved to be particularly effective in cancer treatment, it still remains at cellular level, and research on solid tumors is not common.

According to the investigation of the existing literatures, there are few reports on the direct treatment to an interior of the solid tumor using the low-temperature plasma. In the reported methods, plasma jet is used to irradiate the epidermis near the tumor, or a solution containing plasma as an active substance is injected near the tumor lesion. For the existing apparatus, a plurality of high-voltage electrodes in an array are designed in a quartz tube so as to form a large-area jet under the high-voltage pulse. However, this only increase the treatment area instead of treatment depth. Therefore, it can only treat cancer cells rather than various tumors in vivo, because it is difficult for the low-temperature plasma jet to penetrate the skin.

SUMMARY OF THE INVENTION

This section is to summarize and describe some aspects and embodiments of the invention. Simplifications and omissions may be made in terms of the summary, the abstract and the title to make their purposes clear. These simplifications and omissions are not intended to limit the scope of the application.

In order to overcome the problems in the prior art, the present invention provides a plasma gun for treating a tumor in vivo and a use method thereof.

The plasma gun for treating a tumor in vivo and the use method thereof can address the problem that the low-temperature plasma jet is unable to contact a tumor in vivo. The plasma gun reaches the interior of the tumor, promoting the treatment of the plasma to the tumors. It is suitable for the application in clinical treatment. As compared to the conventional radiotherapy, chemotherapy and surgery, the present invention has the advantages of selectivity on cancer cells and little side effects. The plasma directly reaches the tumor lesion, which has good therapeutic effect and avoids the impact on normal tissues.

The plasma gun for treating a tumor in vivo comprises a generator component including an ionization device and a shield element, and a discharge component. The ionization device is provided at the shield element, and the discharge component is connected to an end of the shield element.

In an embodiment, the discharge component includes a container and an insert. The insert is provided at a tip end of a conical portion of the container.

In an embodiment, the discharge component further includes a gas outlet, and the gas outlet is connected to a side of a cylindrical portion of the container.

In an embodiment, the conical portion and the cylindrical portion are formed as a one-piece structure, and communicate with each other to form an exhaust chamber N.

In an embodiment, the ionization device includes a media supply tube, and one end of the media supply tube is connected to a carrier of the shield element.

In an embodiment, the ionization device further includes a high-voltage central electrode and a low-voltage ring electrode. One end of the high-voltage central electrode is embedded in the carrier. The low-voltage annular electrode is provided at a periphery of a transport body of the shield element.

In an embodiment, one end of the transport body is connected to the carrier, and the other end of the transport body is embedded in the insert.

In an embodiment, the shield element further includes a handle which is provided outside the carrier.

In an embodiment, the transport body and the insert are stainless steel needles, and an oblique opening of the transport body is opposite to an oblique opening of the insert.

A method of treating a tumor in vivo using the plasma gun includes:

adjusting a rotameter to control a flow rate of nitrogen; adjusting an output voltage of a high-voltage RF power supply and monitoring the output voltage, an output current and an output frequency; ejecting a low-temperature plasma formed in an ionization chamber of the plasma gun from the transport body; and inserting the insert of the plasma gun into an interior of the tumor to treat the tumor.

The plasma gun for treating a tumor in vivo and the use method thereof can address the problem that the low-temperature plasma jet is unable to contact a tumor in vivo. The plasma gun reaches the interior of the tumor, promoting the treatment of the plasma to the tumors. It is suitable for the application in clinical treatment. As compared to the conventional radiotherapy, chemotherapy and surgery, the present invention has the advantages of selectivity on cancer cells and little side effects. The plasma directly reaches the tumor lesion, which has good therapeutic effect and avoids the impact on normal tissues. The plasma gun is designed with a simple structure to discharge the exhaust gas in vivo. Such design is minimally invasive to relieve patients' pain and has the advantages of low cost and good exhaust effect. In addition, the oblique openings of the transport body and the insert are concentric stainless steel needles which are provided opposite to each other. Therefore, a space is formed to make the plasma fully contact with the internal tissues of the tumor, promoting the treatment effect.

DETAILED DESCRIPTION OF EMBODIMENTS

The embodiments of the present invention will be further described in detail with reference to the accompanying drawings, from which the object, characteristics and advantages become more apparent and clearer.

In order to make the present invention more understandable, some specific details are illustrated below. The present invention can be implemented in other ways that are not described herein, and similar variations can be made by those skilled in the prior art without departing from the spirit of the present invention. Therefore, the scope of the present invention is not limited to the embodiments below.

The term "embodiment(s)" used herein refers to a particular feature, structure, or characteristic that are included in at least one implementation of the invention. The expression "in an embodiment" described in different places are not necessarily the same embodiment, and are not a separate or alternative embodiment that is mutually exclusive with other embodiments.

Again, the present invention will be described in detail with reference to the accompanying drawings. For illustrative purposes, the sectional view showing the structures of devices is not necessarily to scale. The schematic diagram is only for illustration, which should not limit the scope of the present invention. In addition, the three-dimensional size including length, width and depth should be involved in the practical manufacture.

Figure 1:
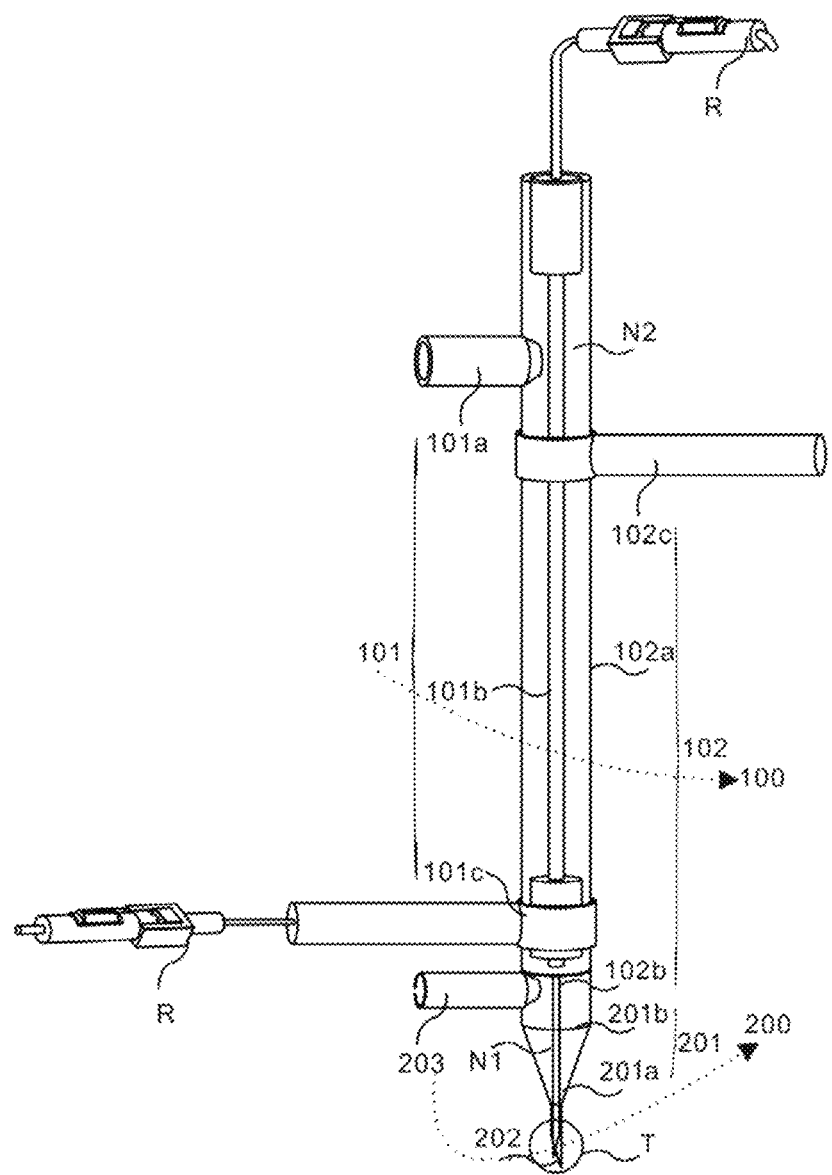
FIG. 1 is a schematic diagram of a plasma gun for treating a tumor in vivo according to a first embodiment of the present invention.

As shown in FIG. 1, the first embodiment provides a plasma gun for treating a tumor in vivo includes a generator component 100 including an ionization device 101 and a shield element 102, and a discharge component 200. The ionization device 101 is provided at the shield element 102, and the discharge component 200 is connected to an end of the shield element 102. The discharge component 200 includes a container 201 and an insert 202 which is provided at a tip end of a conical portion 201*a* of the container 201. The discharge component 200 further includes a gas outlet 203 that is connected to a side of a cylindrical portion 201*b* of the container 201. The conical portion 201*a* and the cylindrical portion 201*b* are formed as a one-piece structure, and communicate with each other to form an exhaust chamber N1. The ionization device 101 includes a media supply tube 101*a*. One end of the media supply tube 101*a* is connected to a carrier 102*a* of the shield element 102. The ionization device further includes a high-voltage central electrode 101*b* and a low-voltage ring electrode 101*c*. One end of the high-voltage central electrode 101*b* is embedded in the carrier 102*a*. The low-voltage ring electrode 101*c* is provided at a periphery of a transport body 102*b* of the shield element 102. One end of the transport body 102*b* is connected to the carrier 102*a*, and the other end of the transport body 102*b* is embedded in the insert 202. The transport body 102*b* and the insert 202 are stainless steel needles. An oblique opening of the transport body 102*b* is opposite to an oblique opening of the insert 202. The shield element 102 further includes a handle 102*c* which is provided outside the carrier 102*a*.

Specifically, the main structure of the present invention includes the generator component 100 and the discharge component 200 which cooperate with each other, enabling the low-temperature plasma jet to directly contact with the tumor in vivo. The plasma gun reaches the interior of the tumor, which promotes the plasma treatment to the tumor. Further, the generator component, comprising the ionization device 101 and the shield element 102, function to carry and generate plasma. An ionization chamber N2 is formed in the shield element 102 for ionization of plasma. The ionization device 101 which is an important component for ionization is provided at the shield element 102. The discharge component 200 that is connected to one end of the shield element 102 can discharge the exhaust in vivo, allowing for a minimally invasive treatment and the relief of patients' pain. In addition, the discharge component 200 has the advantages of low cost and good exhaust effect.

Further, the discharge component 200 includes a container 201 and an insert 202. The insert 202 is provided at a tip end of a conical portion 201*a* of the container 201. The container 201 is adhered to the insert 202 with AB glue to ensure the airtightness at the connection therebetween. The discharge outlet 200 further includes a gas outlet 203. The gas outlet 203 is connected to a side of a cylindrical portion 201*b* of the container 201, and the gas outlet and the cylindrical portion 201b communicate with each other. The gas outlet 203 is a flexible tube or a rigid tube, depending on the requirement for use. preferably, the conical portion 201a and the cylindrical portion 201b are formed as a one-piece structure, and communicate with each other to form an exhaust chamber N1, which provides for removal of the excess exhaust. Preferably, the container 201 is made of a quartz material.

Figure 2:
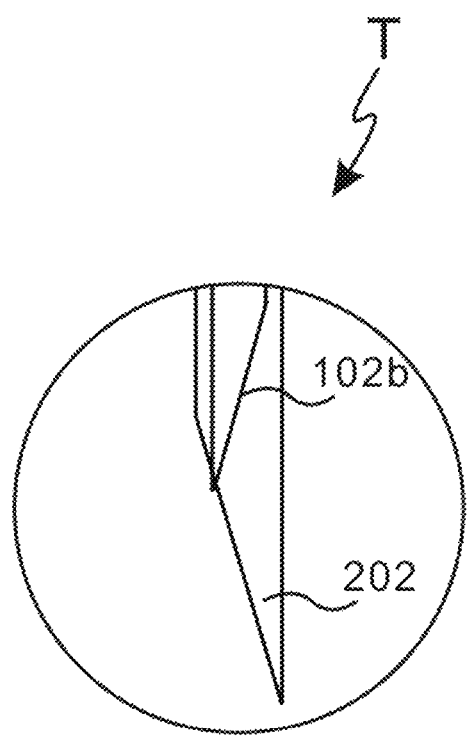
FIG. 2 is an enlarged view of a T portion in FIG. 1.
Figure 3:
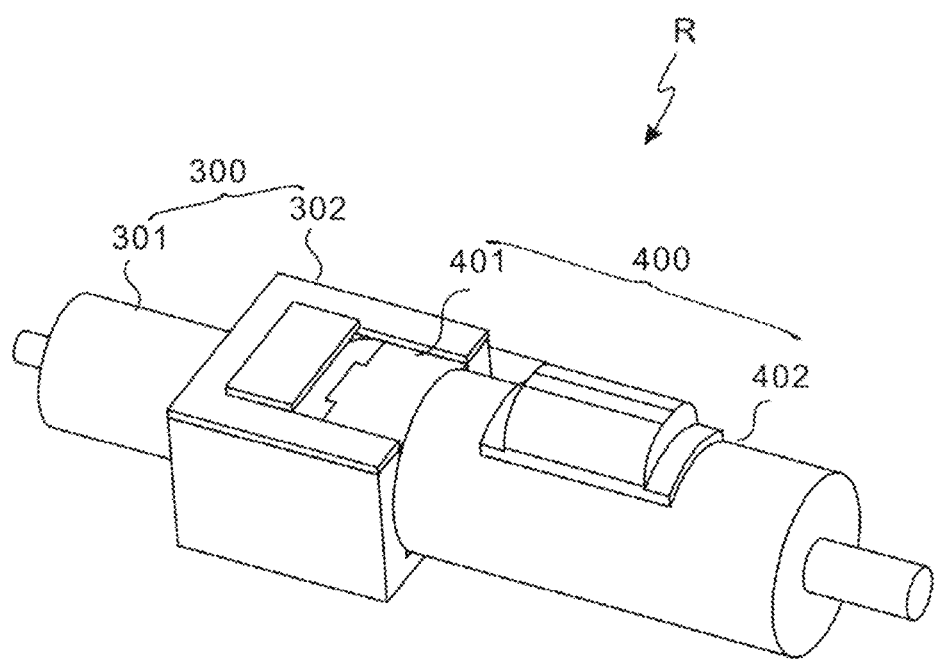
FIG. 3 is a schematic diagram showing a quick connect component according to a second embodiment of the present invention.
Figure 4:
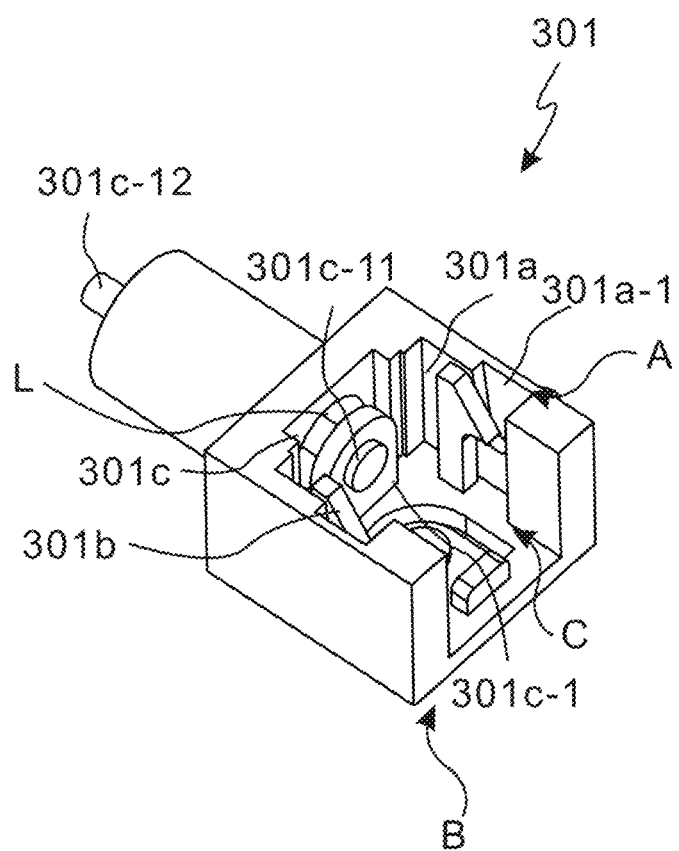
FIG. 4 is a schematic diagram showing a fixing component according to the second embodiment of the present invention.
Figure 5:
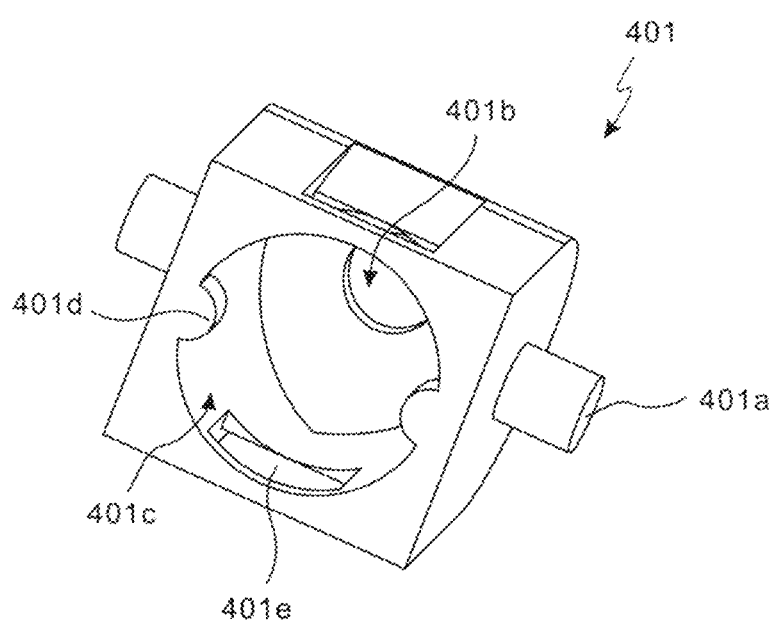
FIG. 5 is a schematic diagram showing a connector according to the second embodiment of the present invention.
Figure 6:
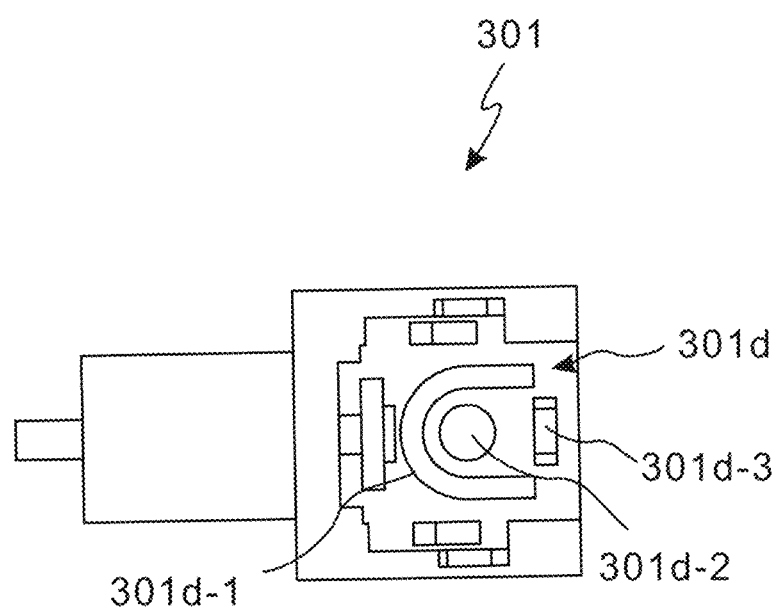
FIG. 6 is a top view of the fixing component according to the second embodiment of the present invention.
Figure 7:
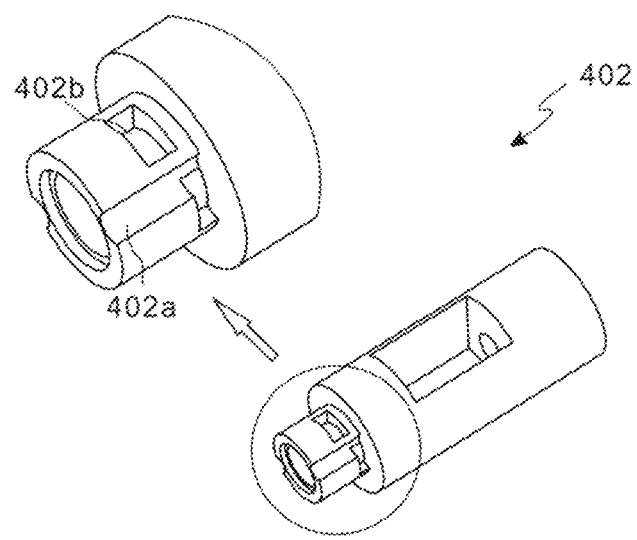
FIG. 7 is a schematic diagram showing a partial structure of a rotation component according to the second embodiment of the present invention.
Figure 8:
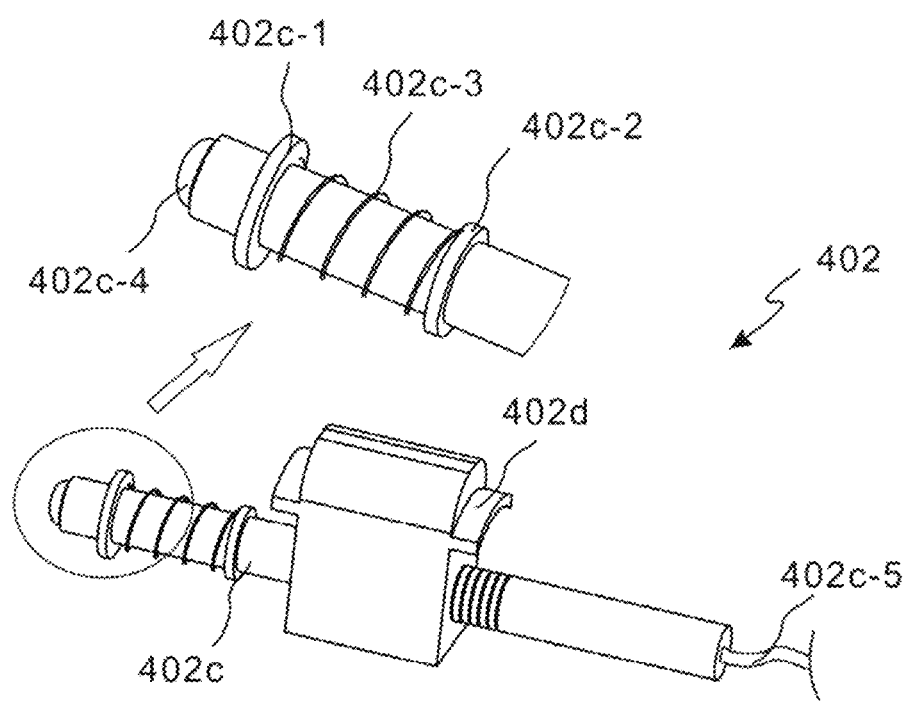
FIG. 8 is a schematic diagram showing another partial structure of the rotation component according to the second embodiment of the present invention.

Further, The ionization device 101 includes a media supply tube 101a. One end of the media supply tube is connected to a carrier 102a of the shield element 102, and they are in communication with each other to transport helium into the ionization chamber N2 for ionization. Preferably, the carrier 102a is a quartz tube. The ionization device 101 further includes a high-voltage central electrode 101b and a low-voltage ring electrode 101c. One end of the high-voltage central electrode 101b is embedded in the carrier 102a, and the low-voltage ring electrode 101c is provided at a periphery of a transport body 102b of the shield element 102. In practical use, the high-voltage central electrode 101b is connected to a high-voltage output end of the high-voltage RF power supply, and the low-voltage ring electrode 101c is connected to a low-voltage output end of the high-voltage RF power supply. The high-voltage central electrode 101b and the low-voltage ring electrode 101c form a electric field, so that the low-temperature plasma is ionized in a safety manner and then is ejected from the transport body 102b. Specifically, one end of the transport body 102b is connected to the carrier 102a by the AB glue, and the other end of the transport body 102b is embedded in an insert 202, namely, the insert 202 is provided at the periphery of the transport body 102b. Preferably, the transport body 102b and the insert 202 are both stainless steel needles in a concentric arrangement. The diameter of the transport body is smaller than that of the insert 202. The oblique opening of the transport body 102 is opposite to the oblique opening of the insert 202 (as shown in FIG. 2), enabling full contact between the plasma and the internal tissues of tumor to promote the treatment; and a space for containing exhaust is formed therebetween as required. The shield element 102 further includes a handle 102c which is provided outside the carrier 102a for the operation purpose.

As shown in FIGS. 3-8, the second embodiment of the present invention is different from the first embodiment in that: the high-voltage central electrode 101b and the low-voltage ring electrode 101c each are connected to the high-voltage RF power supply via a quick connect component R. The quick connect component R includes a positioning member 300 and a quick disconnection member 400 which cooperate with each other to realize a quick connection and disassembly of the high-voltage central electrode 101b and the low-voltage ring electrode 101c.

The positioning member 300 includes a fixing component 301 and a casing 302. The casing 302 is provided on the fixing component 301 comprising an upper surface A and a bottom surface B, and the upper surface A is sunk such that a first holding space C is formed.

The quick disconnection member 400 includes a connector 401 and a rotation component 402. The rotation component 402 is provided in the first holding space C via the connector 401.

The first holding space C includes a first side surface 301a on which a first groove 301a-1 is provided. A first barb 301b is provided at the first side surface 301a opposite to the first groove 301a-1. A hook of the first barb 301b is offset from a bottom of the first groove 301a-1 to form a clamping slot with a central angle greater than 270° for limiting the connector 401.

The first holding space C further includes a second side surface 301c, and a first baffle 301c-1 is provided at a distance of 2-3 mm from the second side surface 301c. The first baffle 301c-1 is parallel to the second side surface 301c. A first conductive copper sheet 301c-11 is provide on the first baffle 301c-1. One end of the first conductive copper sheet 301c-11 is connected to a first wire 301c-12 which sequentially penetrates a through hole L of the fixing component 301 and the first baffle 301c-1.

The connector 401 is hollow where the rotation component 402 is inserted. The connector 401 includes a rotation shaft 401a, a first through hole 401b and a second through hole 401c.

The rotation shaft 401a is clamped at the clamping slot having a central angle greater than 270° formed by the hook of the first barb 301b and the first groove 301a-1.

The first through hole 401b and the second through hole 401c are opposite to each other, and the first through hole 401b cooperates with the first conductive copper sheet 301c-11 to limit the connector 401.

The first holding space C further includes a third side surface 301d, and a second groove 301d-1 and a first protrusion 301d-2 are provided at the third side surface 301d.

When the connector 401 in a horizontal position is anticlockwise rotated by 90° about the rotation shaft 401a, the first protrusion 301d-2 is engaged with the first through hole 401b.

The rotation component 402 is provided with an L-shaped groove 402a at an end where the rotation component 402 and the connector 401 are connected.

The connector 401 further includes a second protrusion 401d extending inwardly from an end of the second through hole 401c to cooperate with the L-shaped groove 402a to limit the position of the rotation component 402.

A fourth through hole 401e is provided on the connector 401, and a third through hole 402b is provided on the rotation component 402.

When the rotation component 402 is inserted into the connector 401, the fourth through hole 401e and the third through hole 402b communicate with each other.

The third side surface 301d is further provided with a fourth protrusion 301d-3 which is just inserted into the fourth through hole 401e and the third through hole 402b.

The rotation component 402 is T-shaped and hollow inside, and is provided with a telescopic rod 402c and a dial block 402d therein. The telescopic rod 402c penetrates through the dial block 402d and is connected to the connector 401.

The telescopic rod 402c includes a front limit spacer 402c-1 and a rear limit spacer 402c-2. An elastic piece 402c-3 is provided between the front limit spacer 402c-1 and the rear limit spacer 402c-2. A second conductive copper sheet 402c-4 is provided at the other end of the limit spacer 402c-1, and one end of the second conductive copper sheet 402c-4 penetrates through the telescopic rod 402c and is connected to the second wire 402c-5.

The front limit spacer 402c-1 is inserted into the rotation component 402 and fixed to the inner wall of the rotation component 402.

The second conductive copper sheet 402c-4 cooperates with the first conductive copper sheet 301c-11.

Specifically, the quick connect component R includes a positioning member 300 and a quick disconnection member

400. The positioning member 300 includes a fixing component 301 and a casing 302, and the casing 302 is provided on the fixing component 301. The casing 302 includes a safety cover, and a flexible cover which is deformable under different use conditions. The safety cover is a concave structure, and the flexible cover is arranged in the concave of the safety cover. Preferably, the hard cover is made of a PVC material, and the flexible cover is made of rubber.

The fixing component 301 comprising upper surface A and bottom surface B has a T-shaped structure, and the upper surface A is sunk such that the first holding space C is formed. The first holding space C includes a first side surface 301*a* and a second side surface 301*c*, and the first side surface 301*a* is provided with a first groove 301*a*-1. A first barb 301*b* is provided at the first side surface 301*a* opposite to the first groove 301*a*-1. It should be noted that in this embodiment, the first groove 301*a*-1 is provided such that the first barb 301*b* possesses some elastic potential energy. One end of the first barb 301*b* is fixed, the other end of the first barb 301*b* is suspended, and the first barb 301*b* is a sheet structure rather than a block. Therefore, the first barb 301*b* may bend in the first groove 301*a*-1 so that it has elastic potential energy to some degree.

Preferably, the hook of the first barb 301*b* is offset from the bottom of the first groove 301*a*-1 to form a clamping slot with a central angle greater than 270°, and the clamping slot limits the connector 401. The "arc" formed by "offset" is reflected in a front view. An arc of the bottom of the first groove 301*a*-1 and the hook of the first barb 301*b* form the arc of greater than 270° for limiting the quick disconnection member 400.

In the first holding space C, a first baffle 301*c*-1 is provided at a distance of 2-3 mm from the second side surface 301*c*. The first baffle 301*c*-1 is parallel to the second side surface 301*c*. A first conductive copper sheet 301*c*-11 is provide on the first baffle 301*c*-1. One end of the first conductive copper sheet 301*c*-11 is connected to a first wire 301*c*-12 which sequentially penetrates a through hole L of the fixing component 301 and the first baffle 301*c*-1, and the other end of the first wire 301*c*-11 is connected to an electrode wire. In this embodiment, there is a gap of 2 to 3 mm between the first baffle 301*c*-1 and the second side surface 301*c*, so as to ensure that the first baffle 301*c*-1 has elastic potential energy to some degree. Similar to the first barb 301*b*, one end of the first baffle 301*c*-1 is fixed and the other end of the first baffle 301*c*-1 is suspended, and the first baffle 301*c*-1 is a sheet structure rather than a block. Therefore, a gap of 2-3 mm is provided between the first baffle 301*c*-1 and the second side surface 301*c*, so that the first baffle has the elastic potential energy to some degree.

The quick disconnection member 400 includes a connector 401 and a rotation component 402. The rotation component 402 is provided in the first holding space C via the connector 401. The connector 401 is hollow inside for inserting the rotation component 402, and the connector 401 includes a rotation shaft 401*a*, a first through hole 401*b* and a second through hole 401*c*. The rotation shaft 401*a* is provided at two opposite sides which are not the two sides provided with the first through hole 401*b* and the second through hole 401*c*. The rotation shaft 401 is clamped at the clamping slot having a central angle greater than 270° formed by the hook of the first barb 301*b* and the first groove 301*a*-1. The first through hole 401*b* and the second through hole 401*c* are opposite to each other, and the first through hole 401*b* cooperates with the first conductive copper sheet 301*c*-11 to limit the connector 401.

The first holding space C further includes a third side surface 301*d*. A second groove 301*d*-1 and a first protrusion 301*d*-2 are provided at the third side surface 301*d*. When the connector 401 in a horizontal position is anticlockwise rotated by 90° about the rotation shaft 401*a*, the first protrusion 301*d*-2 is engaged with the first through hole 401*b*.

It should be noted that the second groove 301*d*-1 is provided to enable the elastic deformation of the baffle on the third side surface 301*d*. Similar to the first baffle 301*c*-1, one end of the baffle on the third side surface 301*d* is fixed, the other end of the baffle is suspended due to the second groove 301*d*-1, and the first baffle 301*c*-1 is a sheet structure rather than a block. Therefore, the baffle has the elastic potential energy to some degree.

In this embodiment, the rotation component 402 and the connector 401 can be easily disassembled. Specifically, the rotation component 402 is provided in the first holding space C via the connector 401. The rotation component 402 is provided with an L-shaped groove 402*a* at an end where the rotation component 402 and the connector 401 are connected. A second protrusion 401*d* extends inwardly from an end of the second through hole 401*c* to cooperate with the L-shaped groove 402*a* to limit the position of the rotation component 402. A third through hole 402*b* is provided at the rotation component 402. When the rotation component 402 is inserted into the connector 401, the fourth through hole 401*e* and the third through hole 402*b* communicate with each other. The third side surface 301*d* is further provided with a fourth protrusion 301*d*-3 which is just inserted into the fourth through hole 401*e* and the third through hole 402*b*.

Preferably, the rotation component 402 is T-shaped and hollow inside, and is provided with a telescopic rod 402*c* and a dial block 402*d* therein. The telescopic rod 402*c* penetrating through the dial block 402*d* is connected to the connector 401. Specifically, the external thread of the telescopic rod 402*c* is coupled with the internal threads of the dial block 402*d*.

Further, the telescopic rod 402*c* includes a front limit spacer 402*c*-1 and a rear limit spacer 402*c*-2. An elastic piece 402*c*-3 is provided between the front limit spacer 402*c*-1 and the rear limit spacer 402*c*-2. A second conductive copper sheet 402*c*-4 is provided at the other end of the limit spacer 402*c*-1, and one end of the second conductive copper sheet 402*c*-4 penetrates through the telescopic rod 402*c* and is connected to the second wire 402*c*-5, and the other end of the second wire 402*c*-5 is connected to the high-voltage RF supply power. The front limit spacer 402*c*-1 is inserted into the rotation component 402 and fixed to the inner wall of the rotation component 402. The second conductive copper sheet 402*c*-4 cooperates with the first conductive copper sheet 301*c*-11 for energization.

During the mounting, the rotation shaft 401*a* is pressed down in the direction from the upper surface A to the bottom surface B, because the first barb 301*b* can be elastically deformed, so that the rotation shaft 401*a* can pass the barb and positioned in the clamping slot where the hook of the first barb 301*b* is offset from the bottom of the first groove 301*a*-1 forming a central angle greater than 270°. Since the barb is curved, the rotation shaft 401*a* cannot be separated from the clamping slot without external force, thereby limiting the rotation shaft 401*a*. Since the rotation component 402 and the connector 401 are connected to each other, they can still be rotated when they are limited. Therefore, the quick disconnection member is fixed through the cooperation of the first through hole 401*b* and the first conductive copper sheet 301c-11. When the quick disconnection member 400 is in a horizontal position, the first conductive copper sheet 301c-11 contacts with the second conductive copper sheet 402c-4 to achieve energization.

In use, if the initial position is in a horizontal position, the second wire 402c-5 is energized, and the current is conducted to the second conductive copper sheet 402c-4 through the second wire 402c-5. In the horizontal position, the first conductive copper sheet 301c-11 is received in the first through hole 401b, and the rotation component 402 and the connector 401 are locked in the horizontal position. When the first conductive copper sheet 301c-11 contacts with the second conductive copper sheet 402c-4, the first conductive copper sheet 301c-11 is energized, and the current is conducted to the electrodes via the first wire 301c-12 to achieve ionization.

Figure 9:
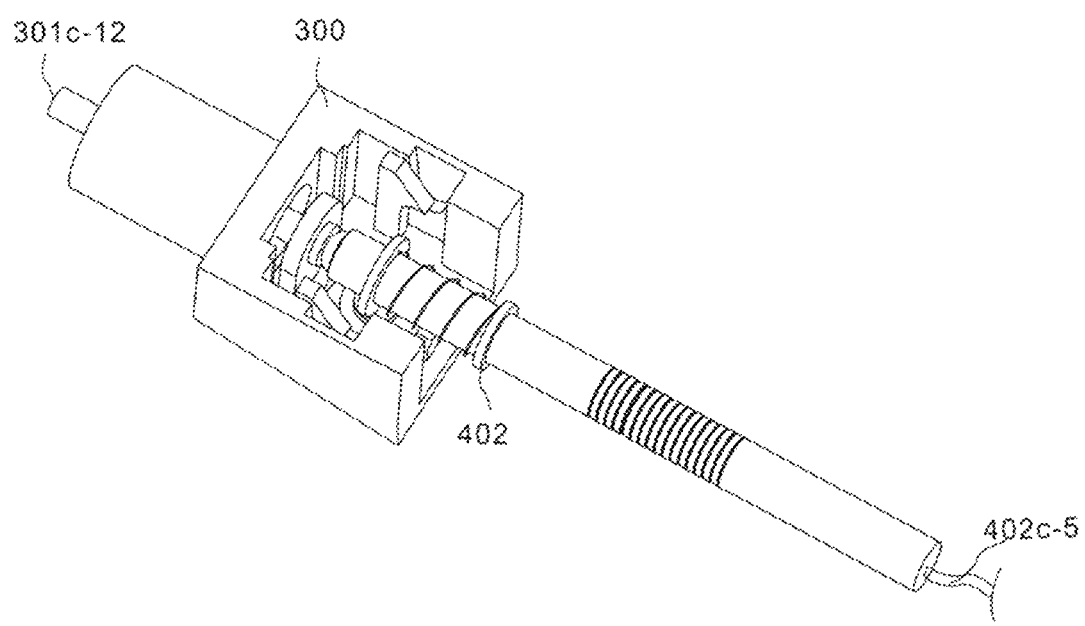
FIG. 9 is a schematic diagram showing the quick connect component in a use state according to the second embodiment of the present invention.
Figure 10:
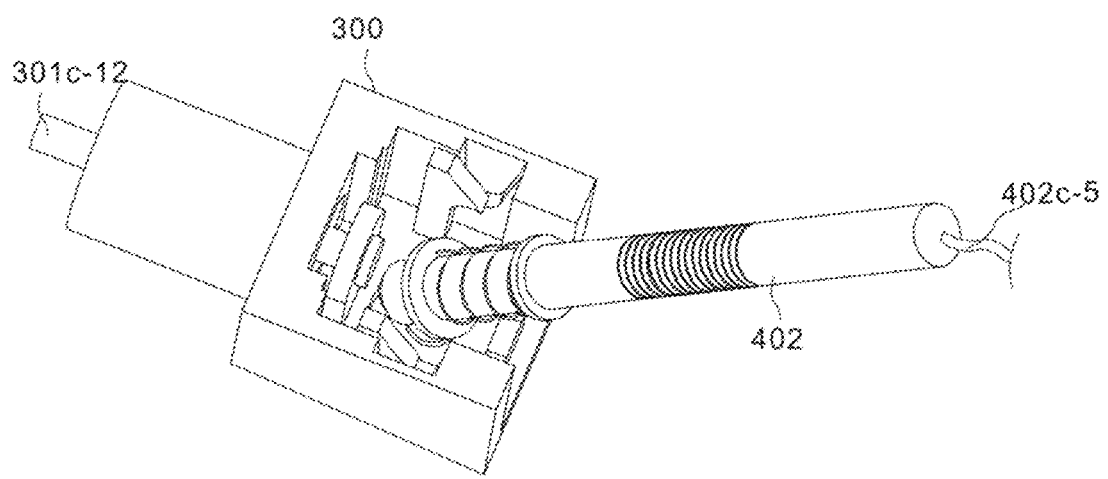
FIG. 10 is a schematic diagram showing the quick connect component in another use state according to the second embodiment of the present invention.

As shown in FIGS. 9-10, when the power supply needs to be disconnected, the dial block 402d protruding on the rotation component 402 is pushed. At this time, since the outer wall of the rotation component 402 is embedded in the periphery of the front limit spacer 402c-1, the telescopic rod 402c abuts against the conductive copper sheet 301c-11, and the quick disconnection member 400 is rotated anticlockwise, so that the first baffle 301c-1 is separated from the first through hole 401b. Since the first baffle 301c-1 has elastic potential energy to some degree, the first baffle 301c-1 will not be broken when rotated, but produces a relative resistance. As a result, the first conductive copper sheet 301c-11 is separated from the second conductive copper sheet 402c-4 to achieve disconnection. The telescopic rod 402c will automatically reset owing to the elastic piece when the pressed telescopic rod 402c is released. After the quick disconnection member is counterclockwise rotated by 90°, the first through hole 401b is engaged with the first protrusion 301d-2, and the quick disconnection member 400 is in a vertical position to allow for a stable disconnection, facilitating the mounting and disassembling. Moreover, the quick disconnection member 400 can be used as a switch to meet the requirements for use.

When the plasma gun is not in use or is to be removed, the quick disconnection member 400 is counterclockwise rotated until the fourth protrusion 301d-3 is separated from the fourth through hole 401e and the third through hole 402b, so that the rotation component 402 can be removed from the connector 401.

Figure 11:
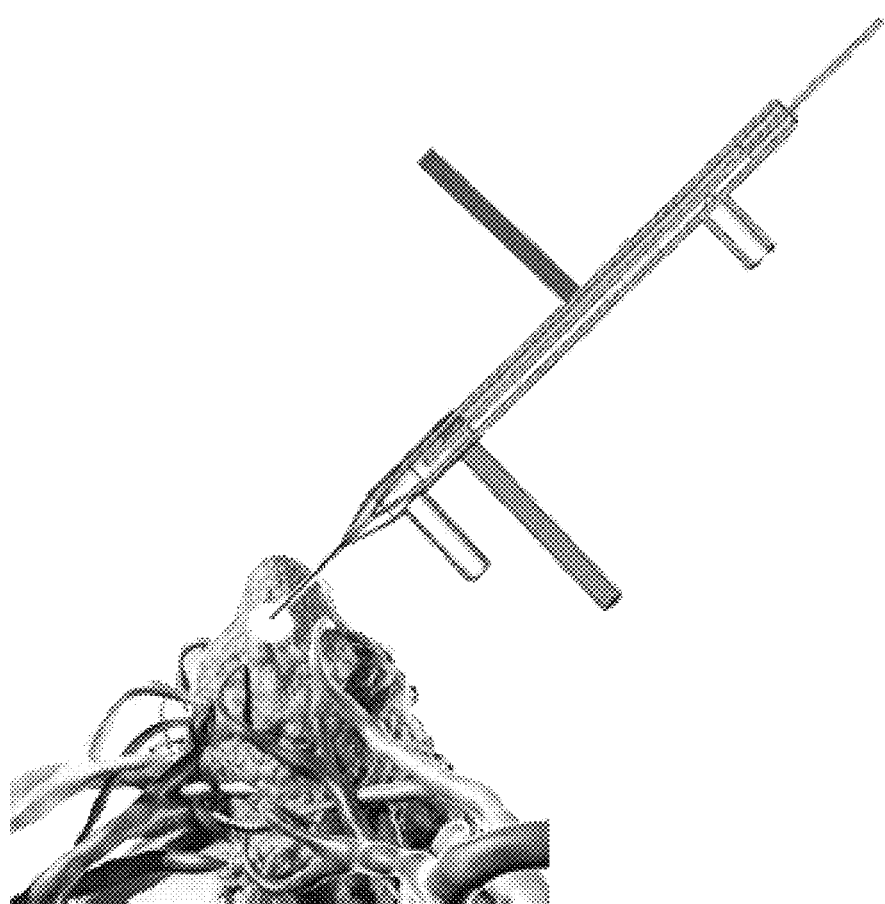
FIG. 11 is a schematic diagram showing a longitudinal cross-sectional structure of treating a tumor by a plasma gun according to a third embodiment of the present invention.
Figure 12:
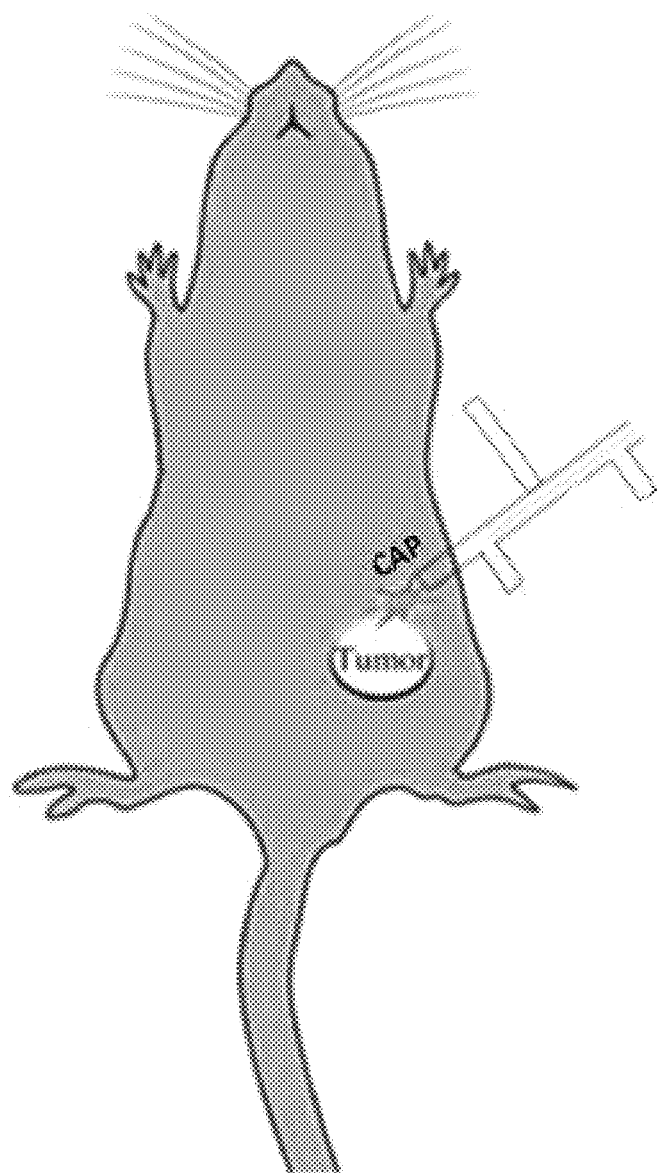
FIG. 12 is a schematic diagram showing operations of the plasma gun in a mouse model according to the third embodiment of the present invention.
Figure 13:
FIG. 13 is a picture showing a mouse with a tumor being treated according to the third embodiment of the present invention.

As shown in FIGS. 11-13, the third embodiment of the present invention provides a method for treating a tumor in vivo using the plasma gun, including the following steps:

adjusting a rotameter to control a flow rate of nitrogen; adjusting an output voltage of a high-voltage RF power supply and monitoring the output voltage, an output current and an output frequency; ejecting a low-temperature plasma formed in an ionization chamber of the plasma gun from the transport body; and inserting the insert of the plasma gun into an interior of the tumor to treat the tumor.

Specifically, helium is introduced from the media supply tube 101a, and the flow rate of the helium is controlled by the rotameter. The high-voltage central electrode 101b and the low-voltage ring electrode 101c each are connected to the high-voltage RF power supply via a quick connect component R. An input voltage, an input current and an input frequency are controlled by an oscilloscope, and the voltage and the frequency are adjusted. An electric field is formed at the high-voltage central electrode 101b and the low-voltage ring electrode 101c. The helium is stably ionized in the ionization chamber N2, and the plasma jet is ejected from the transport body 102b.

The above conditions are maintained for a period of time until the plasma jet is completely stabilized. A mouse is anesthetized and fixed on a lifting platform which is adjusted such that the tumor site in mouse gradually contacts with the insert 202 until the needle is inserted into the tumor. The timer is then started, and the treatment time may be adjusted according to the size of the tumor. When treating a human tumor, the location of the tumors should be checked with the relevant equipment, and then the length of the insert 202 is adjusted, so that the insert 202 is accessible to the interior of the tumor. The treatment for human tumor is similar to the treatment for the mouse tumor.

The specific treating process is as follows. A insulated handle 102c is held, and the insert 202 is slowly approached to the epidermis near the tumor. The epidermis is punctured right above the tumor allowing the insert 202 to enter the tumor. The insert depth is controlled to keep the insert 202 at the center of the tumor, such that the plasma jet of the transport body 102b can directly contact the interior of the tumor in vivo, and excess exhaust can be removed from the body through the special gap between the transport body 102b and the insert 202 to avoid occurrence of swelling. Therefore, the tumor is inhibited.

In the fourth embodiment of the present invention, the high-voltage RF power supply had an output voltage of 0.8 KV and a frequency of 10 KHz; the flow rate of helium was 0.5 SLM; and plasma jet of 2-3 cm in length was ejected from the transport body 102b. The breast cancer cell line SUM149PT was injected into a nude mouse, and when a tumor having a diameter of about 0.5 cm was developed in the nude mouse, the plasma gun was used to treat the tumor according to the operations described above. It was found that after the transport body 102b entered the tumor, there was no swelling around the tumor of the mouse, and the lavender plasma jet was observed in the exhaust chamber. A weak air flow was felt with a hand at the exhaust discharge port, which indicates a good exhaust discharge. When the insert 202 was slowly removed from the mouse body, the plasma jet was normally ejected, indicating that no clogging occurred.

In the fifth embodiment of the present invention, the high-voltage RF power supply had an output voltage of 0.8 KV and a frequency of 10 KHz; the flow rate of helium was 0.5 SLM, and plasma jet of 2-3 cm in length was ejected from the transport body 102b. The breast cancer cell line SUM149PT was injected into nude mice (5 mice for each group), and when a tumor having a diameter of about 0.5 cm was developed in the nude mouse, the plasma gun was used to treat the tumor according to the operations described above. The tumors were treated once a day with a treatment time of 2 minutes. After treated 3 times, the tumors in mice treated by the plasma gun of present invention stopped growing, while the tumors in mice in the negative control group (the insert 202 was inserted into the interior of the tumor in the case where the plasma gun was not energized and only fed with helium) continued to grow. One month later, all mice in the negative control group died, and all mice in the experimental group survived, demonstrating that plasma gun was effective in the treatment of tumors in vivo. The minor wound in the treatment quickly recovered, causing no damage to mice.

It is important to note that the configurations and arrangements of the present application shown in the various embodiments are merely illustrative. Although a few embodiments have been described in detail in this disclosure, those skilled in the art should readily understand that modifications are possible without departing from the novel teachings and advantages of the subject matter described in this application, such as sizes, dimensions, structures, shapes and proportions of various components, as well as parameter values (e.g. temperature, pressure, etc.), arrangements, materials, colors, orientation changes, etc.). For example, an element shown as being integrally formed may be constructed of multiple parts or elements, the position of the elements may be reversed or otherwise altered, and the nature or number or location of the discrete elements may be altered. Therefore, all such modifications are included within the scope of the present invention. The order or sequence of steps of any process or method may be changed or re-sequenced according to alternative embodiments. In claims, any claim of "apparatus with a function" is intended to cover the structure described herein that perform the described function, and are not only structurally equivalent but also equivalent structures. Substitutions, modifications, changes and omissions may be made in the design, operation and arrangement of the embodiments without departing from the scope of the invention. Therefore, the invention is not limited to the specific embodiment, but extends to various modifications that fall within the scope of the appended claims.

In addition, in order to provide a concise description of exemplary embodiments, some features in the embodiments may be omitted (i.e., those that are not related to the best mode for carrying out the invention, or those that are not related to the implementations of the invention).

It should be understood that in the development of any implementations, for example in any engineering or design project, various operations may be made. Such development and effort may be complicated and time-consuming, but for those ordinary skill benefiting from this disclosure, it requires no undue experiments and will be a general operation for design, manufacture and production.

It should be noted that the above embodiments are only used to illustrate the technical solutions of the present invention, and are not intended to limit the technical solutions. Although the invention has been described in detail herein with reference to the preferred embodiments, it should be understood by those skilled in the art that the present invention may be modified or equivalently substituted without departing from the spirit and scope of the invention, which should fall within the scope of the appended claims.

What is claimed is:

1. A plasma gun for treating a tumor in vivo, comprising:
a generator component comprising an ionization device and a shield element, and
a discharge component;
wherein the ionization device is provided at the shield element, and the discharge component is connected to an end of the shield element;
the ionization device comprises a media supply tube, a high-voltage central electrode and a low-voltage ring electrode;
one end of the media supply tube is connected to a carrier of the shield element one end of the high-voltage central electrode is embedded in the carrier; and the low-voltage ring electrode is provided at a periphery of a transport body of the shield element.

2. The plasma gun of claim 1, wherein the shield element further comprises a handle which is provided outside the carrier.

3. A plasma gun for treating a tumor in vivo, comprising:
a generator component comprising an ionization device and a shield element, and
a discharge component;
wherein the ionization device is provided at the shield element; and the discharge component is connected to an end of the shield element;
the discharge component comprises a container, an insert and a gas outlet the insert is provided at a tip end of a conical portion of the container; and the gas outlet is connected to a side of a cylindrical portion of the container;
the ionization device comprises a media supply tube; and one end of the media supply tube is connected to a carrier of the shield element; and
a transport body of the shield element and the insert are stainless steel needles; and an oblique opening of the transport body is opposite to an oblique opening of the insert.

4. The plasma gun of claim 1, wherein the shield element further comprises a handle which is provided outside the carrier.

5. The plasma gun of claim 3, wherein the conical portion and the cylindrical portion are formed as a one-piece structure, and communicate with each other to form an exhaust chamber.

6. The plasma gun of claim 3, wherein one end of the transport body is connected to the carrier, and the other end of the transport body is embedded in the insert.

7. A method of treating a tumor in vivo using a plasma gun, the plasma gun comprising a generator component and a discharge component the generator component comprising an ionization device and a shield element the ionization device being provided at the shield element and the discharge component being connected to an end of the shield element the method comprising:
adjusting a rotameter to control a flow rate of nitrogen; adjusting an output voltage of a high-voltage RF power supply and monitoring the output voltage, an output current and an output frequency; ejecting a low-temperature plasma formed in an ionization chamber of the plasma gun from a transport body of the shield element; and
inserting the insert of the plasma gun into an interior of the tumor to treat the tumor.

* * * * *